(12) United States Patent
Mizobe

(10) Patent No.: US 6,477,888 B1
(45) Date of Patent: Nov. 12, 2002

(54) DEVICE AND METHOD FOR MEASURING MOISTURE PERMEABILITY

(76) Inventor: Kunitaka Mizobe, 1-6-7, Hoshikuma, Jyonan-ku, Fukuoka-shi, Fukuoka (JP)

( * ) Notice: Subject to any disclaimer, the term of this patent is extended or adjusted under 35 U.S.C. 154(b) by 0 days.

(21) Appl. No.: 09/889,720

(22) PCT Filed: Jul. 26, 1999

(86) PCT No.: PCT/JP99/03998

§ 371 (c)(1),
(2), (4) Date: Jul. 18, 2001

(87) PCT Pub. No.: WO00/42411

PCT Pub. Date: Jul. 20, 2000

(30) Foreign Application Priority Data

Jan. 18, 1999 (JP) .......................... 11-009138

(51) Int. Cl.⁷ .............................................. G01N 15/08
(52) U.S. Cl. ........................................................ 73/38
(58) Field of Search .............................. 73/38, 73, 74; 702/30

(56) References Cited

U.S. PATENT DOCUMENTS 4,271,698 A * 6/1981 Wingrave ...................... 73/74
5,299,140 A * 3/1994 Ankeny et al. ............... 702/30

* cited by examiner

Primary Examiner—Hezron Williams
Assistant Examiner—Jay L Politzer
(74) Attorney, Agent, or Firm—Flynn, Thiel, Boutell & Tanis, P.C.

(57) ABSTRACT

A moisture permeability method comprising the steps of measuring the weight of a specimen in constant temperature and humidity room without taking out the specimen from the constant temperature and humidity room to the atmosphere and without being affected by vibration and objectively evaluating the results of the weight measurement by detecting the state of the water vapor permeating a sample and the temperature of stored water; a moisture permeability measuring device, wherein a precision electronic scale (7) is installed on a damoing stand (6) set in the constant temperature and humidity room (P), the weight of the specimen (T) in which the sample (2) is installed on a measuring cup (1) containing water (W) is measured by the precision electronic scale and the measured results are converted into a moisture permeability, the measuring cup (1) comprising a cup main body (10) and a retaining ring (11), thermocouples (40) immersed in water being installed through the peripheral wall part of the cup main body, and a temperature—humidity sensor (41) being attached to extend to a space (15) between the water surface and the sample.

8 Claims, 8 Drawing Sheets

DEVICE AND METHOD FOR MEASURING MOISTURE PERMEABILITY

FIELD OF THE ART

The present invention relates to a device and a method for measuring a moisture permeability used to measure moisture permeability features of a permeable film and other paper, cardboard, and fabric products provided in a device for removing water vapor used for dehumidification in a frame.

BACKGROUND OF THE ART

The moisture permeability test method for fabric products according to JIS LI099 is known as a conventional method for measuring a moisture permeability.

A method A-2 according to JIS L1099 is a water method wherein a specific amount of water is poured into a moisture permeation cup, then a specimen is formed by mounting a packing and the ring with a sample set on the moisture permeation cup.

Said specimen is stored in a specified constant temperature/humidity room, then the specimen is taken out to measure a weight after a specified time (primary measurement process) and the specimen is stored in the constant temperature/humidity room again, then the specimen is taken out to measure a weight after the specified time again (secondary measurement process).

Thereafter, a difference obtained from subtracting a value of the secondary measurement from a value of the primary measurement is converted into a moisture permeability.

Furthermore, the moisture permeability measuring device wherein the sample is clamped between an upward cup and a downward cup and temperatures and humidity of spaces in both cups are measured before and after permeation of water vapor, then, from the result of this measurement, a moisture permeability of the sample is measured in principle is known.

However, in said water method according to JIS L1099, the specimen need be taken out from the constant temperature/humidity room into the atmosphere each time the primary measurement process and the secondary measurement process is performed. Thus, the sample is much affected by an atmospheric temperature and humidity and a temperature and humidity on the surface of the sample are changed by moving wind blown onto the surface of the sample along with mounting and dismounting the specimen such that an error easily occurs in a measurement result and a reliability is poor.

Furthermore, for the moisture permeability measuring device of the latter, a measurement result greatly depends on a precision of a sensor, a measurement result differs by a sensor error at a moisture permeability measurement requiring precision, and especially, there is a problem that a measurement error caused by an aged deterioration of the sensor easily occurs.

The present invention is done to solve the above-mentioned problem, and the subject is to provide the device and method for measuring a moisture permeability comprising the steps of measuring a weight of a specimen in the constant temperature/humidity room without taking the specimen from the constant temperature/humidity room to the atmosphere without being affected by vibration and objectively evaluating the results of the weight measurement by detecting the state of the water vapor permeating a sample and the temperature of stored water.

In addition, measurements under an influence of a difference between surface temperatures of the water vapor exhaust port and the water vapor supply port of a sample and an influence of an electric charge of a sample will be enabled.

DISCLOSURE OF THE INVENTION

To solve the aforementioned problem, the moisture permeability measurement device according to the present invention comprises:

a precision electronic balance is installed on a damping stand (shock absorbing stand) in a constant temperature/humidity room;

low viscosity resin such as silicone or epoxy resin is permeated into a peripheral part of a measuring cup containing water;

a packing part is formed by resin such as silicon rubber or epoxy resin on the top and bottom of the peripheral part;

furthermore, the weight of a specimen in which a sample having the packing part filled with resin such as non-fluid silicone or epoxy resin covering the peripheral surface is measured by said precision electronic balance; and the measuring cup has the cup main body with the open top and a retaining ring that clamps the sample between itself and the top of the cup main body by a specific fastening pressure; and thermocouples immersed in water stored in the cup main body are installed through the peripheral wall part of the cup main body and a temperature-humidity sensor is installed to extend to a space between the water surface and the sample.

Moreover, a water supply and drain passage opened/closed by a valve is formed in the bottom of the cup main body and a water level drainage opened/closed by a drain valve is installed below the temperature-humidity sensor on the peripheral wall part of the cup main body.

Furthermore, the moisture permeability measurement device according to the present invention comprises:

an embodiment showing a perforated plate is installed in the vicinity of the sample on the vapor exhaust port of the sample;

another embodiment showing that said perforated plate is selected from multiple types of perforated plates having different thermal conduction speeds; and another embodiment showing that the perforated plate is grounded.

Furthermore, the moisture permeability measuring method according to the present invention uses the moisture permeability measuring device wherein;

a specimen in which the sample is clamped between the top of the cup main body storing water and the retaining ring with a specific fastening pressure;

the specimen is installed on the precision electronic balance installed on the damping stand in the constant temperature-humidity room;

in this state, the weight of the specimen is measured for a specific time and results are converted into a moisture permeability based on a difference between a weight at the start of the measurement and a weight after the specific time is passed; and at the same time, a water temperature is measured with the lapse of time and a temperature and humidity of a space in the specimen is measured by the temperature-humidity sensor.

Furthermore, the moisture permeability measurement method according to the present invention comprises:

an embodiment showing a moisture permeability is measured with or without a perforated plate installed in the vicinity of the sample on the vapor exhaust port of the sample; and furthermore, another embodiment shows that a moisture permeability is measured with or without a perforated plate grounded.

BEST MODE FOR CARRYING OUT THE INVENTION

Embodiments of the present invention will be explained with reference to drawings.

Figure 1:
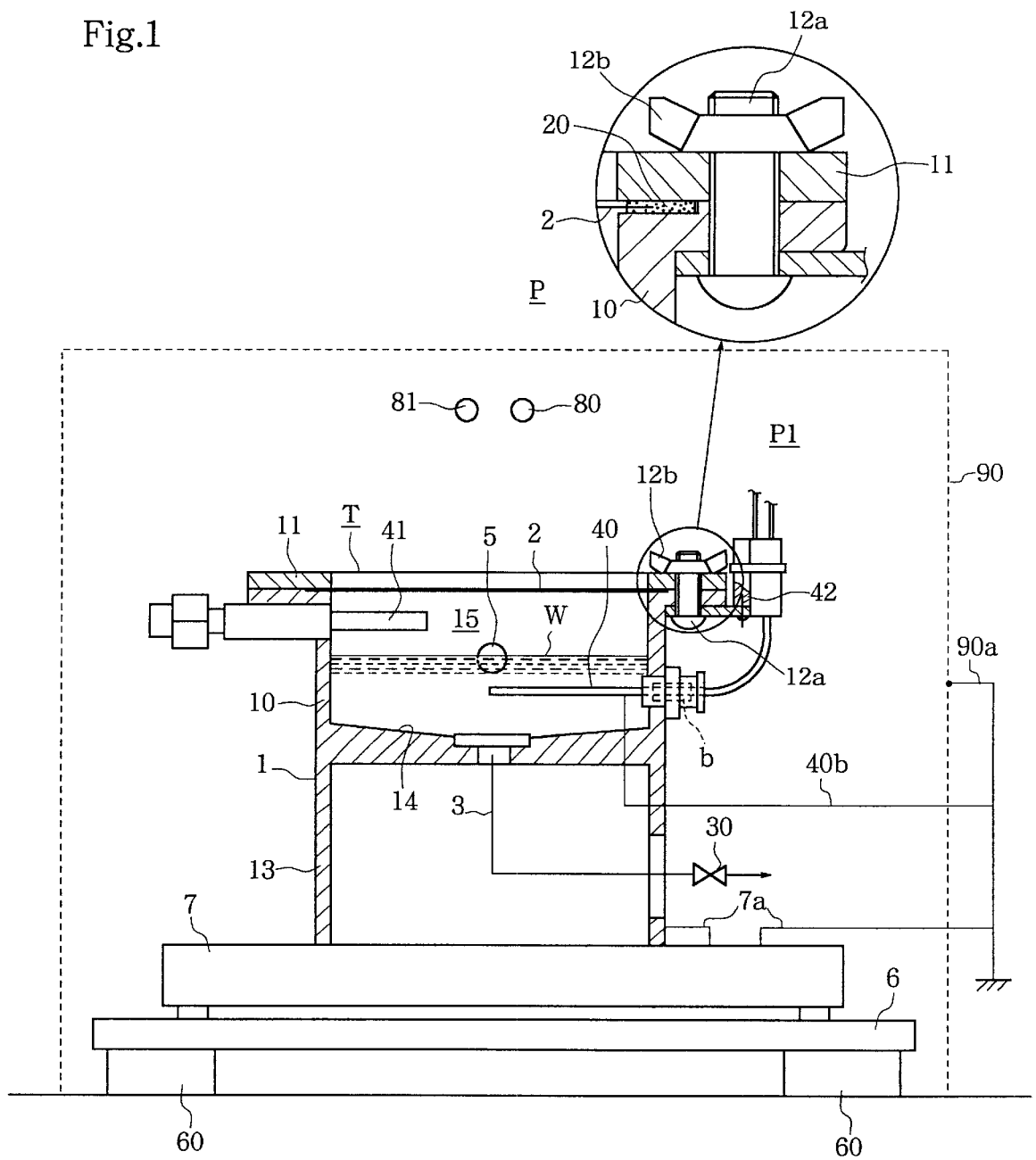
FIG. 1 is a cross-sectional view of the moisture permeability measuring device according to the first embodiment.
Figure 2:
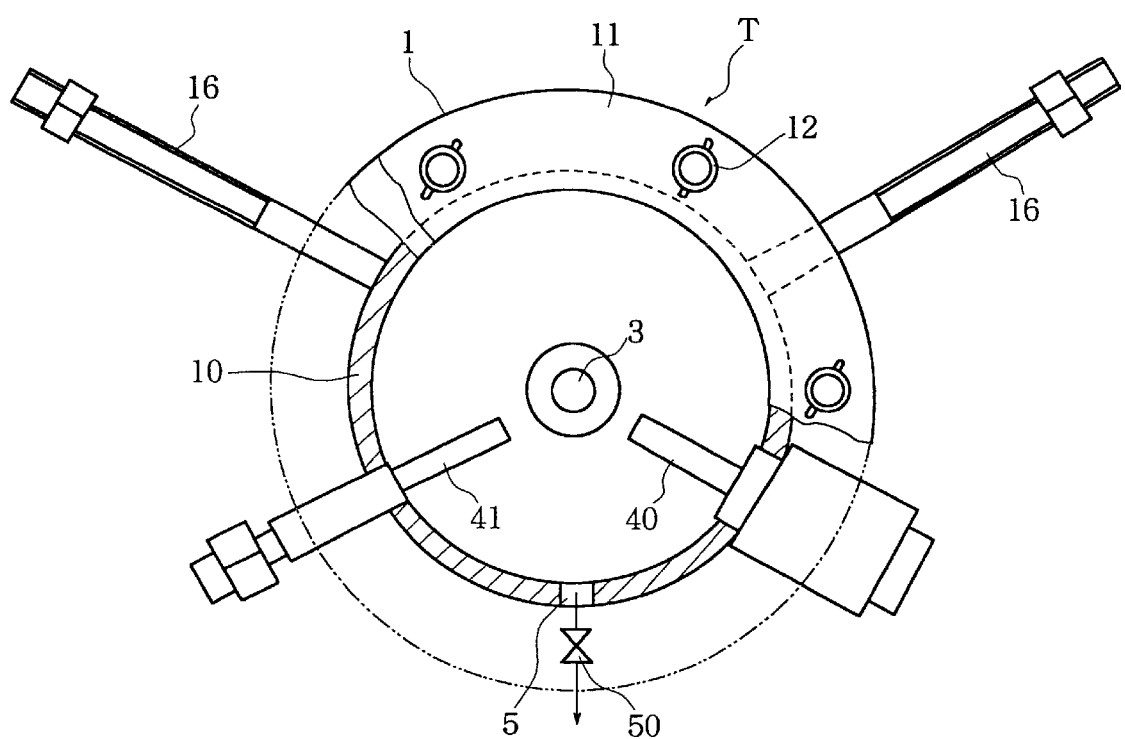
FIG. 2 is the notched plain view showing the main body of the measuring cup used for said moisture permeability measuring device.
Figure 3:
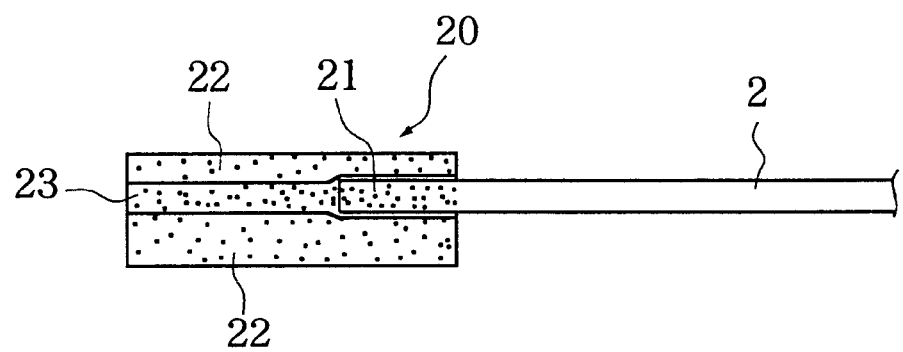
FIG. 3 is the expanded cross-sectional view showing the seal part of the sample.

FIG. 1 is the cross-sectional view of the moisture permeability measuring device according to the first embodiment, and FIG. 2 is the notched plain view showing the main body of the measuring cup used for the moisture permeability measuring device.

In the figure, numeral 1 designates the measurement cup comprising the cup main body 10 having the opened top and the retaining ring 11. The specimen T is formed by setting the sample 2 between the top of the cup main body 10 storing the water W (pure water) and the retaining ring 11, then securing the sample 2 with a bolt 12a and a wing nut 12b.

In addition the seal part 20 is attached on the peripheral part of said sample 2 to prevent air leakage. In this seal part 20, a low viscosity (=40 Pa/s) silicone 21 is permeated into the peripheral part and packing parts 22 and 22 made of silicone rubber are formed on the top and bottom of the peripheral part, and moreover, non-fluid silicone 23 is filled up between the packing 22 and 22 to cover the surface of the peripheral part of the sample 2. However, for the seal part 20 of the sample, the silicone need not always be used, but epoxy resin can also be used.

Said seal part 20 is installed so that it can be stored in a level difference part 10a formed by level differences smaller than the thickness of the seal part 20 on the top of the cup main body 10. That is, because the seal part 20 is made of silicone, it has a high elasticity, and therefore, when the seal part 20 is fixed by the retaining ring 11 with an excessive force, it swells sideward and the sample 2 is loosened. The loosening of the sample 2 affects a moisture permeability, and when fastening pressures of the retaining ring 11 are uneven in repeated measurements, measured values also become uneven, and therefore, the fastening pressure of the retaining ring 11 need be made constant.

Therefore, the provided level difference part 10a is used as a stopper to make fastening pressure of the retaining ring 11 constant. In addition, a means to adjust the fastening pressure such as an adjustable bolt can also be provided instead of the level difference part 10a.

Said cup main body 10 comprises a skirt part 13 so that the a bottom is raised and a bottom surface is formed on a surface of a falling gradient toward a center, and a water supply and drain passage 3 opened/ closed by a valve 30 is formed in the deepest part of the center.

Thermocouples 40 immersed in water W stored in the cup main body 10 is installed through the peripheral wall part of the cup main body 10 and a temperature-humidity sensor 41 is attached to extend to a space 15 between the water W and the sample 2 to measure a temperature and humidity.

In this case, the center part of the thermocouples 40 is installed through the peripheral wall part of the cup main body 10 through a rubber bushing b and a base end part of the thermocouples 40 is attached to a mounting material 42 made of aluminum fastened together on the flange part of the cup main body 10 with a bolt 12a. Thus, by attaching the thermocouples 40 through the mounting material 42 having a high thermal conduction speed, a heat transfer from the cup main body 10 to the thermocouples 40 is improved, a temperature of the thermocouples 40 can be approximated to a temperature of the cup main body 10 very quickly, and therefore, an error in measurement using the thermocouples 40 can be reduced.

Moreover, a water level adjustment drainage 5 opened/ closed by drain valve 50 is installed below said temperature-humidity sensor 41 on the peripheral wall part of the cup main body 10. In addition, numeral 16 in the figure designates a balancer fixed on the peripheral wall part of the cup main body 10 to adjust the center gravity to be a center of a measuring cup 1.

Thereafter, the weight of said specimen T is measured in a constant temperature/humidity room set to a specific temperature and humidity, and the measured value is converted into a moisture permeability.

In this case, a wind shield net 90 made of a perforated body used to keep a wind velocity in a measurement space P1 to a constant velocity or less is installed to cover the moisture permeability measuring device in the constant temperature/humidity room P.

In said measurement space P1 the damping stand 6 wherein a vibration absorbing material 60 is set in a bottom is installed, a precision electrical balance 7 that can measure up to 1 g/10,000 is installed on said damping stand 6, and a specimen T will be set on said precision electronic balance 7. In addition, numeral 80 in the figure designates a temperature/humidity sensor installed in the measurement space P1, and numeral 81 designates an senometer.

Furthermore, numeral 7a designates a conductor to ground the cup main body 10 and the precision electronic balance 7, numeral 40b designates a conductor to ground the thermocouples 40, and numeral 90a designates a conductor to ground the wind shield net 90. Therefore, because the precision electronic balance 7 is grounded, the cup main body 10 is grounded when being installed on the precision electronic balance 7.

Furthermore, because the wind shield net 90 is grounded, the space 15 in the cup and the measurement space P1 easily become the same potential and hard to be charged. By this feature, an electrolytic corrosion on the cup main body 10 hardly occurs.

Furthermore, although it is not illustrated in the figure, an elevator unit is installed in the measurement space P1 to support a specimen T.

Catching material is installed along a guide installed in the measurement space P1 so that said elevator unit can move up and down, and on the other hand, a protruded support material is installed on the cup main body 10, and the specimen T is set so that said support material is supported by the catching material. Thereafter, the catching material is lowered with said specimen T set to mount the specimen T onto the precision electronic balance 7, then the catching material is furthermore lowered to separate the specimen T from the support material.

By the above-mentioned operation, the specimen T can gently be installed onto the precision electronic balance 7 without giving any shock to the specimen T and the precision electronic balance 7.

In addition, elevation of the catching material in the elevator unit can be driven manually or using an electrical motor, air cylinder, or hydraulic cylinder. As a means for power transfer, a wire, chain, gear, or link can be used. A combination of these driving means and power transfer means composes the elevation mechanism of the catching material.

Thereafter, a moisture permeability measuring method using said moisture permeability measuring device will be explained.

According to said moisture permeability measurement method, a specimen T is first created and water W (pure water) is stored in the cup main body 10 at the beginning.

At this time, when the water W need be supplied or drained, valve 30 is opened to supply or drain the water W from the water supply and drain passage 3. In addition, a water level is adjusted from the water level drainage 5 opened/closed by the drain valve 50.

By the above-mentioned feature, an appropriate amount of water W can be stored in the cup main body 10 without wetting the temperature-humidity sensor 41 with water.

The water W is thus stored in the cup main body 10, then the specimen T is formed by setting a sample 2 between the top of the cup main body 10 and the retaining ring 11 and fix the specimen 2 with a bolt 12a and a wing nut 12b. At this time, leakage of water vapor from the peripheral part of the sample 2 is surely prevented by the seal part 20.

Thereafter, a measurement is performed with the sample T set in the measurement space P1 of the constant temperature/humidity room to prevent an error in a measurement result caused by a change in a temperature or humidity of the atmosphere because the sample 2 is easily affected by a temperature and humidity.

In addition, the sample T is installed on the precision electronic balance 7 with said catching material, but when the specimen T is carried before the specimen T is supported by the catching material, the specimen T need be carried at a horizontal level so that the sample 2 is not wet with the water W, and for this purpose, an exclusive lift unit is used to carry the specimen T being hanged down.

Thereafter, the constant temperature/humidity room is closed after the specimen T is installed onto the precision electronic balance 7 as described above, then a measurement is performed by remote control. In this case, as shown in FIG. 4, measurement data of the temperature-humidity sensor 41 and the thermocouples 40 is fetched into an external computer device 85 by cables 41a and 40a, and so the cables 41a and 40a are connected beforehand when the specimen T is supported on the catching material.

Types of said cables 41a and 40a are selected and laid so that weights of the cables 41a and 40a do not affect weight measurement of the specimen T. In this case, use cables having excellent portability and extensibility (e.g., Mobiron manufactured by Yoshinogawa Cable Col., Ltd.) for the cables 41a and 40a and connected with a connector 87 by bundling into a fan shape or reverse cone shape right above the center of the specimen T so that a cyclic elastic vibration hardly occurs.

Figure 4:
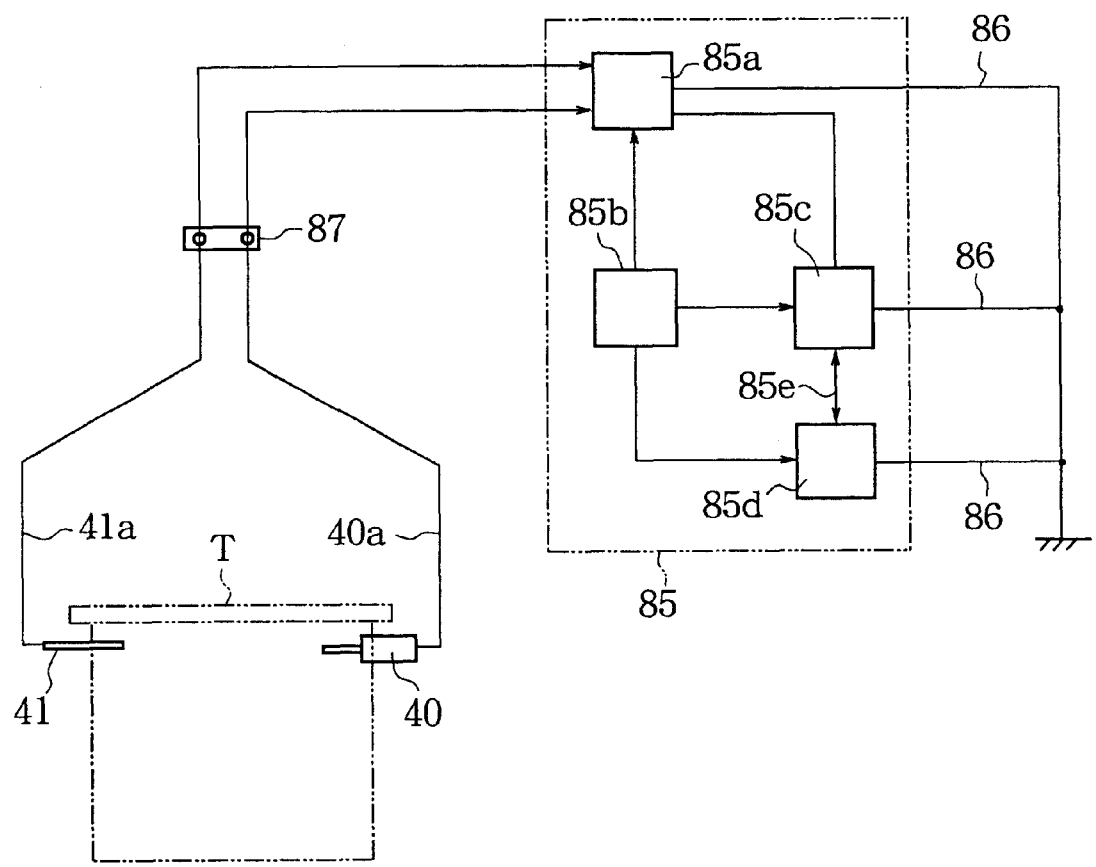
FIG. 4 is the explanatory drawing showing an electrical cable laying of the moisture permeability measuring device.

In addition, in FIG. 4, numeral 85a designates a converter unit, numeral 85b designates a power supply, numeral 85c designates a storage logger, numeral 85d designates a personal computer, and numeral 85e designates an transmission cable (RS232C). In addition, grounding cables 86 are connected to the converter unit 85a, the storage logger 85c, and the personal computer 85d.

When a measurement is started, the precision electronic balance 7 on which the specimen T installed is first set to zero.

Thereafter, in this state, the weight of the specimen T is measured for a specific time (1 hour) with the lapse of time and a difference between a weight at the start of the measurement (set to zero) and a weight measured after the specific time is passed is converted into a moisture permeability and, at the same time, a water temperature is measured with the lapse of time using the thermocouples 40 together with measuring a temperature and humidity of a space 15 in the specimen T with the temperature-humidity sensor 41.

In addition, the following formula is used to convert a weight difference of the specimen T into a moisture permeability:

$$P = 10 \times (A2 - A1)/S$$

where;

P: Moisture permeability (g/m2/h)

A2−A1: Amount of a change in a weight of a specimen per a specific time unit (mg/h)

S: Moisture permeability area (cm2)

Figure 5:
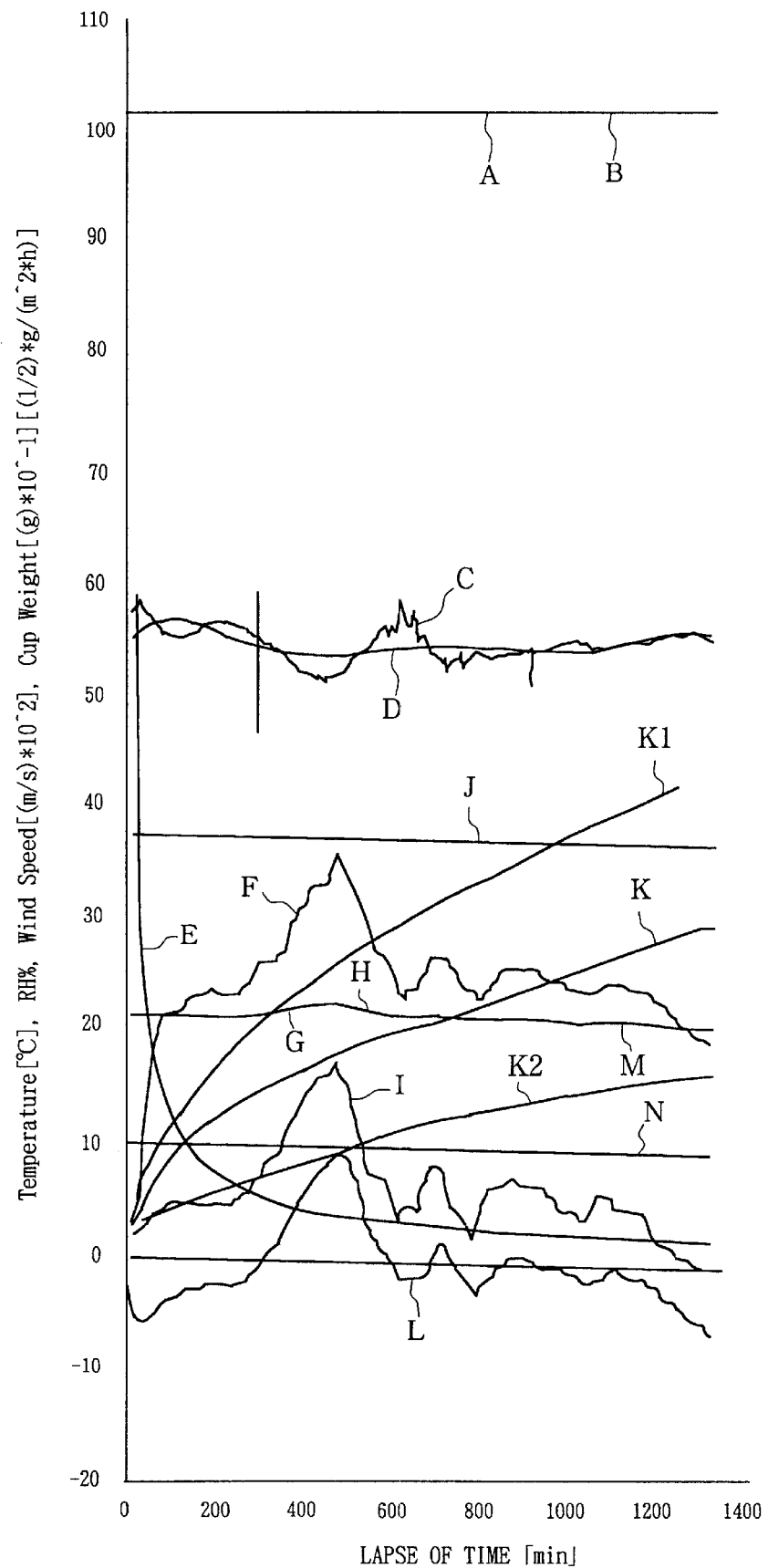
FIG. 5 is the graphic representation showing results of the measurement using the moisture permeability measuring device.

In addition, FIG. 5 is the graphic representation showing a result of a measurement of a sample having a seal part made of epoxy resin having a small elasticity by using the moisture permeability measuring device.

In the figure:

A designates a relative humidity in a cup;

B designates a relative humidity in a polynomial cup;

C designates a relative humidity of a measurement space;

D designates a relative humidity of a polynomial measurement space

E designates a moisture permeability;

F designates an amount of variance of water in a cup ×10;

G designates a water temperature in a cup:
P.17/48

H designates a measurement space temperature;

I designates an amount of variation of a measurement space temperature ×10;

J designates a cup weight ×10−1;

K designates an amount of variance of a cup weight ×102×0.5;

L designates an amount of variance of a temperature in a cup ×10;

M designates a temperature in a cup; and

N designates a wind velocity in a measurement space ×102

In addition. in the graph showing amounts of variances F, I, K and L, a weight J, and a wind velocity of N, original values are multiplied by 10−1 to 0.5×102 to seize variance states in details and to indicate the values in one graph.

According to said moisture permeability measuring method, the specimen T is created in the atmosphere as aforementioned, but the series of measurements can all be performed in the constant temperature/humidity room P (measurement room P1).

Therefore, the weight of the specimen T can be measured without taking out the specimen T from the constant temperature/humidity room P (measurement room Pl) to the atmosphere and can also be measured precisely in an environment without a vibration.

Furthermore, to measure a temperature and humidity of the space 15 in the specimen T with the temperature-humidity sensor 41 together with measuring a water temperature with the lapse of time using the thermocouples 40, a state of water vapor permeating the sample 2 can be seized.

By the above-mentioned feature, a result of measuring a weight can objectively be evaluated based on results of these measurements related to water vapor and a precise and reliable measurement is enabled.

Furthermore, when air leaks from a pinhole on the sample 2 or the seal part 20, the amount of variance of the cup weight K shows a sharp inclinations in the graphic representation shown in FIG. 5 and air leakage from the sample 2 or the seal part 20 can be detected from said sharp inclination.

Furthermore, in the graphic representation shown in FIG. 5, an unevenness of a temperature caused by rise of the amount of the water temperature in the cup F after the start of the measurement, but when the thermocouples 40 is attached through the mounting material 42 made of aluminum having a high thermal conduction speed as aforementioned, a heat transfer from the cup main body 10 to which the water temperature is reflected to the thermocouples 50 is improved to eliminate the unevenness of the temperature by approximating the temperature of the thermocouples 40 to the temperature of the cup main body 10 very quickly.

Figure 6:
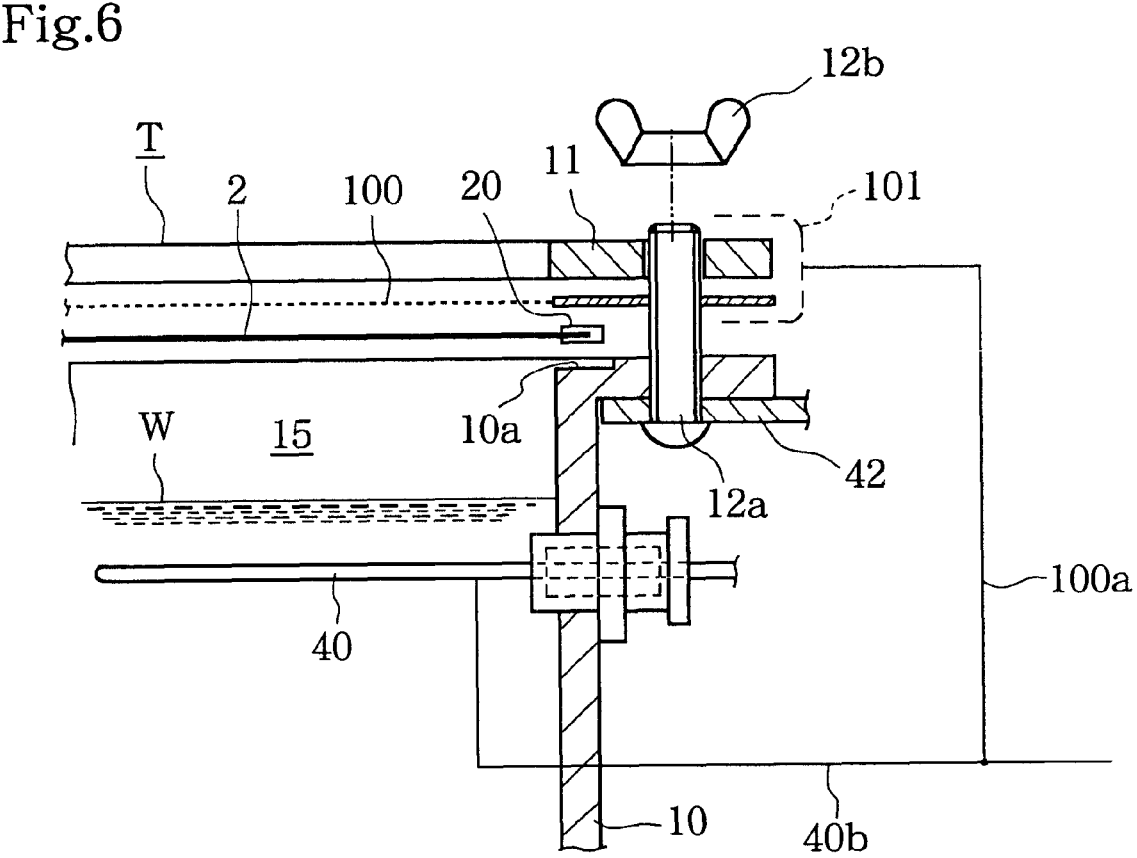
FIG. 6 is the exploded cross-sectional view showing main parts of the moisture permeability measuring device according to the second embodiment.

Thereafter, FIG. 6 is the exploded cross-sectional view showing main parts of the moisture permeability measuring device according to the second embodiment.

In said moisture permeability measuring device, a perforated plate 100 is installed in the vicinity of the sample 2 on the vapor exhaust port of the sample 2. In this case, the specimen T is formed by piling up the sample 2 and the perforated plate 10 between the top of the cup main body 10 and the retaining ring 11 and fastening together with a bolt 12a and a wing nut 12b.

Thereafter, said perforated plate 100 was selected from multiple types of perforated plates having different thermal conduction speeds such as mesh plates of aluminum, copper, platinum, and stainless steel having high thermal conduction speeds or a resin mesh plate having a low thermal conduction speed. In addition, passivation processing is applied to the surface of the perforated plate 100.

Furthermore, in said moisture permeability measuring device, a conductive net 101 is sandwiched between the perforated plate 100 and the wind nut 12 and the net 101 and a conductor 40b are interconnected with a conductor 100a to ground the perforated plate 100.

A permeable film or other material to be the sample 2 is used for various purposes in various places and may be installed in a place with different temperatures separated by a thin film or other material as a boundary. To deal with such use, it is a matter of course that an essential moisture permeability of the sample need be measured accurately and also, a moisture permeability need be measured in a state where a difference between surface temperatures of a vapor supply port and a vapor exhaust port of the sample 2 is deliberately set.

To accurately measure an essential moisture permeability of the sample, surface temperatures of the vapor supply port and the vapor exhaust port of the sample 2 are required to be the same. However, the surface temperature of the vapor supply port of the sample 2 is affected by heat transfer from a measuring cup 1 and, on the other hand because the surface temperature of the vapor exhaust port of the sample 2 is affected by a temperature of a temperature of the measurement space P1, there is a difference between surface temperatures on the vapor supply port and vapor exhaust port of the sample 2.

Therefore, when a perforated plate having a special high thermal conduction speed (e.g., copper mesh plate) is selected and used as the perforated plate 100 as aforementioned, the perforated plate 100 is affected by heat transfer from the measuring cup 1 and, as a result, the surface temperatures of the vapor supply port and the vapor exhaust port of the sample 2 can be made the same. Furthermore, when a perforated plate having a high thermal conduction speed is used, heat conduction with the measuring cup 1 through the bolt 12a can be obtained, and so a temperature difference from the inside of the cup can be minimized.

Therefore, when moisture permeability is measured in the above-mentioned state, an essential moisture permeability of the sample can be measured accurately. In addition, a standby time necessary for sufficient heat transfer from the measuring cup 1 to the perforated plate 100 is prepared for measurement On the other hand, to seize a moisture permeability corresponding to use conditions of the thin film to be the sample 2, a moisture permeability need be measured with a difference between the surface temperatures on the vapor supply port and vapor exhaust port deliberately set.

In such case, a moisture permeability can be seized when there are various temperature differences between the vapor supply port and the vapor exhaust port of a specific sample 2 by preparing several types of perforated plates 100 having different thermal conduction speeds and measuring moisture permeability by using these perforated plates 100.

In addition, an amount of variation of a cup weight ×102×0.5 in the case of using a copper mesh plate having a specially high thermal conduction speed as the perforated plate 100 is shown as K1 in the graphic representation shown in FIG. 5, and an amount of variation of a cup weight ×102×0.5 in the case of using a resin mesh plate having a special low thermal conduction speed as the perforated plate is shown as K2 in the graphical representation shown in FIG. 5. In this case, when a measurement result is K1, the moisture permeability of E shifts upward, and when a measurement result is K2, the moisture permeability of E shifts downward.

Furthermore, when a perforated plate 10 is charged, the static electricity keeps water drops adhered on the sample 2 and these water drops hinder accurate measurement of an essential moisture permeability of the sample. Therefore, when perforated plate 100 is grounded, the electrical charge of the sample 2 is relaxed and a moisture permeability can be measured accurately by eliminating the hindrance by the adhered water drops.

Furthermore, when a moisture permeability of the sample 2 is measured, a moisture permeability when the perforated plate 100 is charged need also be seized. In such case, a moisture permeability can be measured when the perforated plate 100 is charged by deliberately disconnecting the grounding of the perforated plate 100.

Furthermore, because the thermal conductivity and electrical conductivity of the perforated plate 100 are almost proportional, basic data for adjusting move of water vapor can be collected together with performing electrolytic relaxation of the sample 2.

Figure 7:
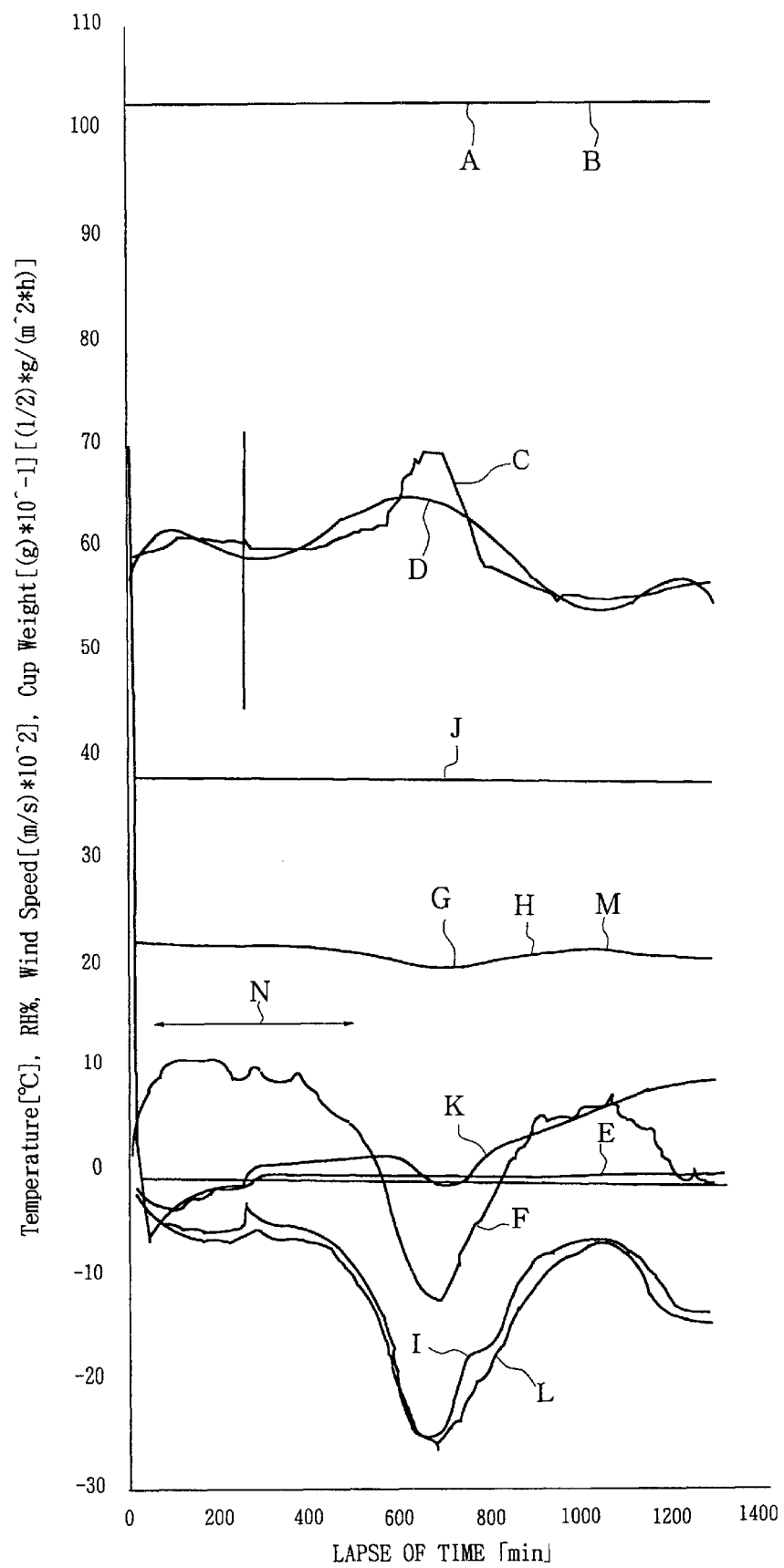
FIG. 7 is the graphic representation showing results of the measurement using the moisture permeability measuring device.
Figure 8:
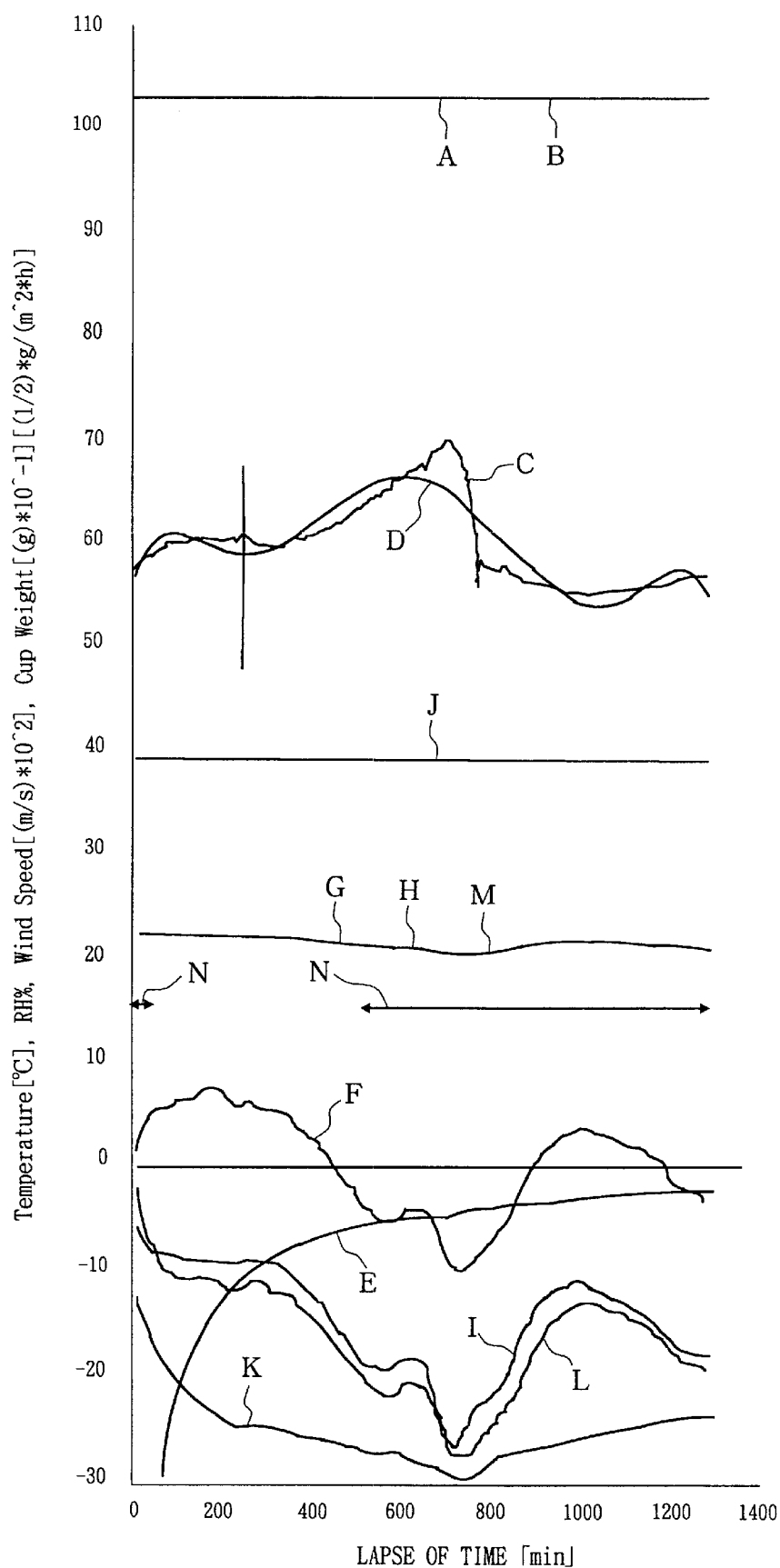
FIG. 8 is the graphic representation showing results of the measurement using the moisture permeability measuring device.

Thereafter, FIGS. 7 and 8 are the graphic representations showing results of measurements using the moisture permeability measuring device with the perforated plate installed.

In these figures, symbols designating graphs are the same as those of said FIG. 5. FIGS. 7 and 8 show measurement results used to compare influences by winds flown in the measurement space P1.

A temperature of a sample and temperature distribution need be made constant for measurement, and for this purpose, an atmospheric temperature and temperature distribution are preferably even with regard to the measurement space P1.

When a wind velocity in the measurement space P1 is raised, the unevenness of the atmospheric temperature and the temperature distribution can be eliminated by mixing of air, but on the other hand, an accurate measurement is impossible because a precision electronic balance 7 shakes by an influence of a wind and the sample is also blown by the wind.

On the other hand, when a wind velocity in the measurement space P1 is lowered, an influence to the precision electronic balance 7 can be eliminated, but because air is not much mixed, an accurate measurement is impossible because an unevenness occurs in the atmospheric temperature and the temperature distribution.

Therefore, the temperature of the sample and the temperature distribution are desired to be made constant while lowering the wind velocity in the measurement space Pl so that the wind does not affect the precision electronic balance 7, and therefore, a perforated plate 100 having a high thermal conduction speed is installed in the vicinity of the sample on the vapor exhaust port and the temperature of the sample and the temperature distribution are made even while preventing the sample from being blown by the wind.

In addition, wind is blown within the range from the start to the halfway of the measurement in the graphic representation shown in FIG. 7, and wind is blown within the range from the start and halfway to the end of the measurement in the graphic representation shown in FIG. 8. As it can be understood from these figures, because the amount of variance of the cup weight K (moisture permeability E) differs depending on how the wind is blown even when the perforated plate 100 is installed, the relationship between how the wind is blown and the amount of variance of the cup weight K (moisture permeability E).

A concrete configuration is not limited to the embodiments of the present invention so-far explained with reference to drawings.

An influence to a moisture permeability feature when perforated plates having different thickness features and physical properties can precisely and actually be measured.

For example, a precise measurement using a perforated plate having the thick center and thin peripheral part or a perforated plate having a low thermal conduction speed in the center and a high thermal conduction speed in the peripheral part is possible.

FIELD OF THE INVENTION

As so-far explained, the following effects can be obtained according to the present invention:

Because the precision electronic balance is installed on the damping stand, a specimen can be measured on the precision electronic balance without being affected by a vibration.

Furthermore, because the precision electronic balance is installed in the constant temperature/humidity room, the weight of the specimen can be measured in the constant temperature/humidity room without an influence of taking out to the atmosphere.

Furthermore, because the temperature-humidity sensor and the thermocouples are installed, a state of water vapor permeating the sample can be seized. By the above-mentioned feature, a result of a weight measurement can be objectively evaluated based on these measurement results related to water vapor, and thus a precise and highly reliable measurement is enabled.

In addition, water can be supplied or drained and a water level can be adjusted without wetting the temperature-humidity sensor by opening the water supply and draining passage and the water level adjustment drainage.

Furthermore, because the water supply and drain passage and the water level adjustment drainage are provided so that water can be supplied or drained and a water level can be adjusted without wetting the temperature-humidity sensor, the temperature-humidity sensor can be prevented from being damaged by water.

Furthermore, because low viscosity resin such as silicone or epoxy resin is permeated into the peripheral part of the sample and packings are formed by resin such as silicone rubber or epoxy resin on the top and bottom of the peripheral part, and moreover, resin such as non-fluid silicone or epoxy resin is filled up between the packings to cover the peripheral part of the sample and the sample is clamped by the retaining ring with a specific fastening pressure, air leakage can be prevented surely, and because the sample is not loosened, unevenness in measured values can be prevented.

What is claimed is:

1. A moisture permeability measuring device which comprises:

a precision electronic balance installed on a damping stand (shock absorbing stand) installed in a constant temperature/humidity room;

a measuring cup having a peripheral part and a water containing part;

low viscosity resin permeated into said peripheral part of said measuring cup;

a packing part formed by resin on the top and bottom of the peripheral part;

a specimen formed by setting a sample having a seal part formed by filling with resin covering the peripheral surface; and said measuring cup having a cup main body with an open top and a retaining ring that clamps the seal part of said sample between itself and a level difference part, said level difference part comprising level differences smaller than the thickness of said seal part and being formed on the top of the cup main body;

thermocouples immersed in water stored in the cup main body and installed through the peripheral wall part of the cup main body;

a temperature-humidity sensor extending to a space between the water surface and the sample;

a water supply and drain passage opened/closed by a valve in the bottom of said cup main body; and a water level drainage opened/closed by a drain valve installed below said temperature-humidity sensor on the peripheral wall part of the cup main body.

2. The moisture permeability measuring device according to claim 1 wherein:

a perforated plate is installed in the vicinity of the sample on a vapor exhaust port of the sample.

3. The moisture permeability measuring device according to claim 1, wherein said perforated plate is selected from multiple types of perforated plates having different thermal conduction speeds.

4. The moisture permeability measuring device according to claim 3, wherein the perforated plate is grounded.

5. The moisture permeability measuring device according to claim 2, wherein said low viscosity resin consists of one of silicone and epoxy resin, said packing part resin consists of one of silicon rubber and epoxy resin, and said seal part resin consists of one of non fluid silicone and epoxy resin.

6. A moisture permeability measuring method comprising:

providing a specimen including a sample having a seal part;

forming a level difference part, comprising level differences smaller than the thickness of said seal part of the sample, on the top of a cup main body storing water with a specific fastening pressure;

installing said specimen on a precision electronic balance installed on a damping stand in a constant temperature-humidity room;

measuring the weight of the specimen for a specific time and noting results;

converting said results into a moisture permeability based on a difference between a weight at the start of the measurement and a weight after the specific time is passed; and at the same time, measuring a water temperature with a lapse of time and measuring a temperature and humidity of a space in the specimen by a temperature-humidity sensor.

7. The moisture permeability measuring method according to claim 6, including providing a perforated plate installed in the vicinity of the sample on a vapor exhaust port of the sample.

8. The moisture permeability measuring method according to claim 6, including providing a grounded perforated plate.

* * * * *